(12) United States Patent
Limaye et al.

(10) Patent No.: US 11,744,956 B2
(45) Date of Patent: Sep. 5, 2023

(54) MEDICAL SHARP REMOVAL AND STORAGE DEVICE

(71) Applicant: Becton, Dickinson and Company, Franklin Lakes, NJ (US)

(72) Inventors: Amit Limaye, Wayne, NJ (US); David Schiff, Highland Park, NJ (US); Eric Chang, East Brunswick, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 914 days.

(21) Appl. No.: 16/628,970

(22) PCT Filed: Jun. 22, 2018

(86) PCT No.: PCT/US2018/039030
§ 371 (c)(1),
(2) Date: Jan. 6, 2020

(87) PCT Pub. No.: WO2019/010017
PCT Pub. Date: Jan. 10, 2019

(65) Prior Publication Data
US 2020/0222640 A1  Jul. 16, 2020

Related U.S. Application Data

(60) Provisional application No. 62/529,926, filed on Jul. 7, 2017, provisional application No. 62/530,001, filed on Jul. 7, 2017.

(51) Int. Cl.
*A61M 5/32* (2006.01)
*H05B 6/06* (2006.01)
(Continued)

(52) U.S. Cl.
CPC ......... *A61M 5/3205* (2013.01); *A61B 50/362* (2016.02); *B09B 3/00* (2013.01);
(Continued)

(58) Field of Classification Search
CPC .................. A61M 5/3205; A61M 2005/3209
(Continued)

(56) References Cited

U.S. PATENT DOCUMENTS 3,753,412 A   8/1973  Shepard et al.
4,268,364 A   5/1981  Hall
(Continued)

FOREIGN PATENT DOCUMENTS

CN   104185327 B    2/2016
IT   MO20130014 A1  7/2014
(Continued)

*Primary Examiner* — Jacob K Ackun
(74) *Attorney, Agent, or Firm* — Dickinson Wright PLLC

(57) ABSTRACT

An apparatus for entirely removing a medical sharp from a holder to which it is connected, including a body (102), a heating unit (104) disposed in the body, a receiving unit (114) fixedly disposed in the body and configured to receive the holder, and a collet (122) movably disposed within the body and configured to receive the medical sharp. The apparatus also includes a first biasing member (130) disposed within the body, and a user interface (136) coupled to the collet and configured to displace the collet away from the receiving unit, actuate the first biasing member to increase a bias on the collet toward the receiving unit, and actuate the heating unit.

24 Claims, 21 Drawing Sheets

(51) Int. Cl.
*H05B 6/10* (2006.01)
*H05B 6/36* (2006.01)
*A61B 50/36* (2016.01)
*B09B 3/00* (2022.01)

(52) U.S. Cl.
CPC .............. *H05B 6/06* (2013.01); *H05B 6/101* (2013.01); *H05B 6/36* (2013.01); *A61B 2050/364* (2016.02); *A61M 2005/3206* (2013.01); *A61M 2005/3209* (2013.01); *A61M 2205/50* (2013.01); *A61M 2205/8206* (2013.01); *A61M 2205/8243* (2013.01)

(58) Field of Classification Search
USPC ................................. 206/366; 29/426.5, 700
See application file for complete search history.

(56) References Cited

U.S. PATENT DOCUMENTS

| | | | |
|---|---|---|---|
| 4,614,035 A | 9/1986 | Andrews | |
| 4,867,309 A | 9/1989 | Germain | |
| 5,076,178 A | 12/1991 | Kohl et al. | |
| 5,212,362 A | 5/1993 | Burden et al. | |
| 5,277,868 A | 1/1994 | Langford | |
| 5,441,622 A | 8/1995 | Langford | |
| 5,545,869 A | 8/1996 | Piva | |
| 5,616,136 A * | 4/1997 | Shillington | A61M 5/344 604/240 |
| 5,727,455 A | 3/1998 | Yerman | |
| 5,761,975 A | 6/1998 | Waluda | |
| 5,852,267 A | 12/1998 | Yanobu | |
| 5,968,402 A | 10/1999 | Lee | |
| 6,545,242 B1 | 4/2003 | Butler | |
| 7,001,472 B2 | 2/2006 | Collier et al. | |
| 7,513,363 B2 | 4/2009 | Brown | |
| 7,971,715 B1 | 7/2011 | Fernandes et al. | |
| 8,829,394 B2 | 9/2014 | Limaye | |
| 8,882,706 B2 | 11/2014 | Cronenberg | |
| 9,579,469 B2 | 2/2017 | Limaye | |
| 9,802,006 B2 | 10/2017 | Limaye | |
| 2005/0121343 A1 | 6/2005 | Miller et al. | |
| 2006/0118553 A1 | 6/2006 | Terada et al. | |
| 2007/0215578 A1 | 9/2007 | Ito et al. | |
| 2009/0014462 A1* | 1/2009 | Costa | A61M 5/3205 221/185 |
| 2009/0178943 A1 | 7/2009 | Oostman, Jr. et al. | |
| 2012/0311839 A1 | 12/2012 | Limaye | |
| 2016/0175542 A1 | 6/2016 | Kirby et al. | |
| 2018/0200455 A1* | 7/2018 | Ahmadi | A61M 5/3278 |

FOREIGN PATENT DOCUMENTS

| | | |
|---|---|---|
| JP | H06505178 A | 6/1994 |
| JP | 200125493 A | 1/2001 |
| JP | 2004202112 A | 7/2004 |
| JP | 2007259891 A | 10/2007 |
| JP | 2013512727 A | 4/2013 |
| JP | 2014518746 A | 8/2014 |
| JP | 2016525005 A | 8/2016 |
| WO | WO-2012169993 | 12/2012 |
| WO | WO-2015011443 A2 | 1/2015 |

* cited by examiner

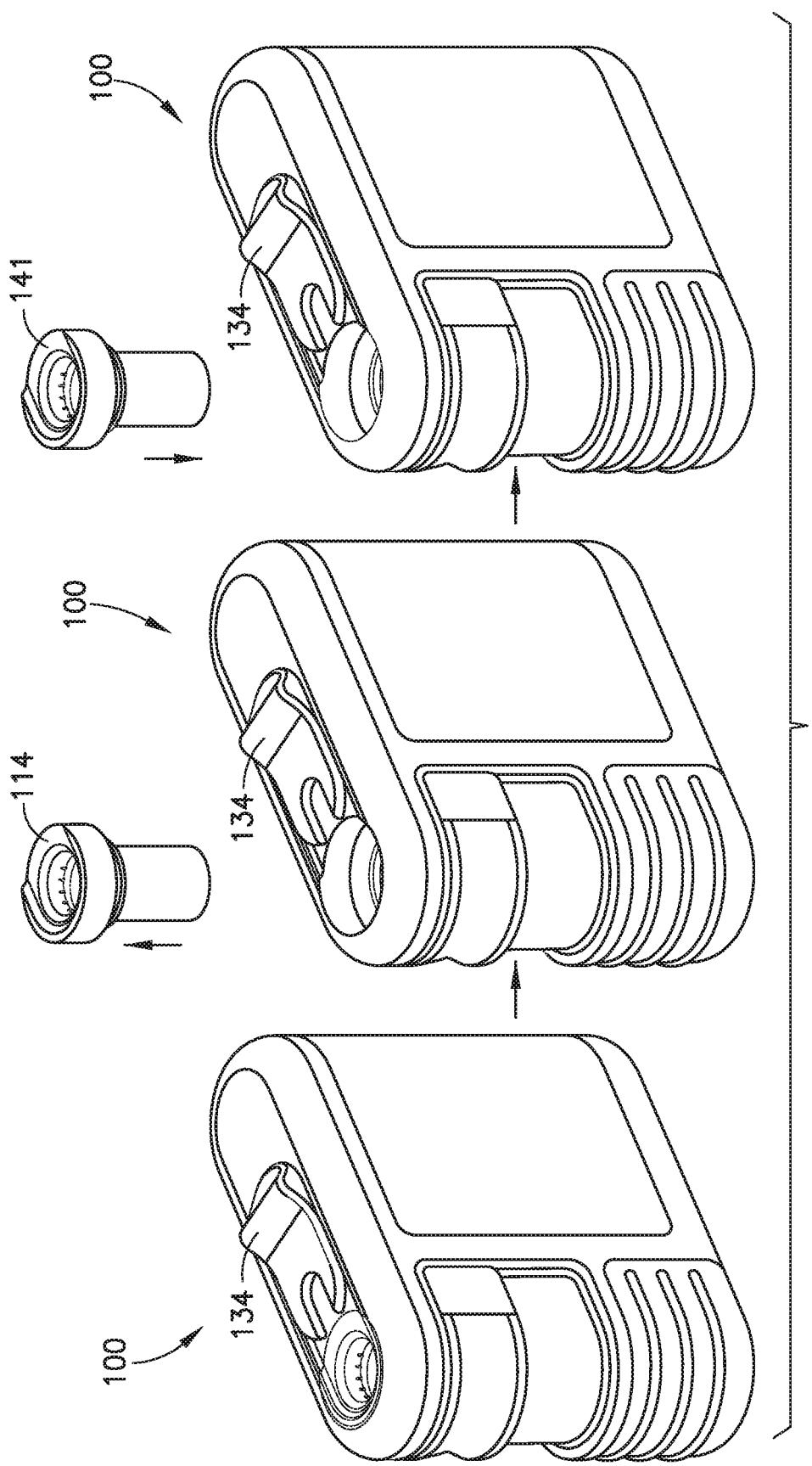

MEDICAL SHARP REMOVAL AND STORAGE DEVICE

CROSS-REFERENCE TO RELATED APPLICATION

This application claims priority to U.S. Provisional Patent Application Ser. No. 62/529,926, filed on Jul. 7, 2017 and entitled "Medical Sharp Removal and Storage Device", and to U.S. Provisional Patent Application Ser. No. 62/530,001, filed on Jul. 7, 2017 and entitled "Induction Heating Circuit for Medical Sharps Removal Device", the entire disclosures of both of said applications being expressly incorporated herein by reference.

FIELD OF THE INVENTION

The present invention relates generally to a device for entirely removing a medical sharp from a holder and storing the removed medical sharp.

BACKGROUND OF THE INVENTION

After a medical sharp, such as a hypodermic needle or a pen needle, has been used for an injection it is desirable to remove and dispose of the needle in a safe container for several reasons. For example, the medical sharp often dulls after a single use, so subsequent use may cause discomfort to the patient. Additionally, multiple use of the medical sharp can also reduce the strength of the sharp, which may cause a potential fracture. Further, medical sharp reuse increases sanitary concerns and health risks to the patient. Moreover, exposed medical sharps can pose a health risk to patients, caregivers, and waste management workers.

A sharps container for storing needles, which is known in the art, includes an inner box member and an outer housing member. The box and the housing each have an aperture that is dimensioned to receive a hypodermic needle. The box and the housing are hingedly connected to each other so that in an open position the apertures of the box and the housing overlap and the needle may be inserted through both of the apertures to project into the box. After the needle has been inserted into the apertures, the box and the housing are moved with respect to each other, for example in a scissor motion, so that the needle is clipped. After being clipped, the needle drops into the box for storage and subsequent disposal. Traditionally, the sharps container is a large red box, and insertion of the medical sharps is relatively easy, but removal of the medical sharps therefrom is purposefully difficult.

U.S. Pat. No. 6,545,242 to Butler discloses a device that, subsequent to insertion of a portion of a needle, heats at least a portion of the needle to approximately 1750° C., and then shears the needle, leaving a portion in the needle holder or hub. Similarly, U.S. Pat. No. 5,545,869 to Piva discloses a device that melts a portion of a blade or needle and cuts the stump of the blade or needle, leaving a portion of the blade or needle in the needle/blade holder or hub. Additionally, U.S. Pat. No. 4,867,309 to Germain discloses a device that holds a needle and its holder or hub by the needle stem, so that a user can twist the hub off of a syringe, or pull off the hub if the hub is friction-fitted on the syringe.

With each of these devices, however, a portion of the needle remains in the needle holder. Therefore, the potential for a needle-stick injury may remain. Additionally, the needle holder must be disposed of as medical waste, and cannot be recycled. Consequently, an improved medical needle removal device that removes the needle entirely is desirable. Storage of the removed needles is also desirable.

BRIEF DESCRIPTION OF THE DRAWINGS

Aspects and advantages of embodiments of the invention will be more readily appreciated from the following detailed description, taken in conjunction with the accompanying drawings, in which:

FIG. 21 illustrates the receiving unit of the device of FIG. 1 being replaced.

SUMMARY OF EMBODIMENTS OF THE INVENTION

Figure 1:
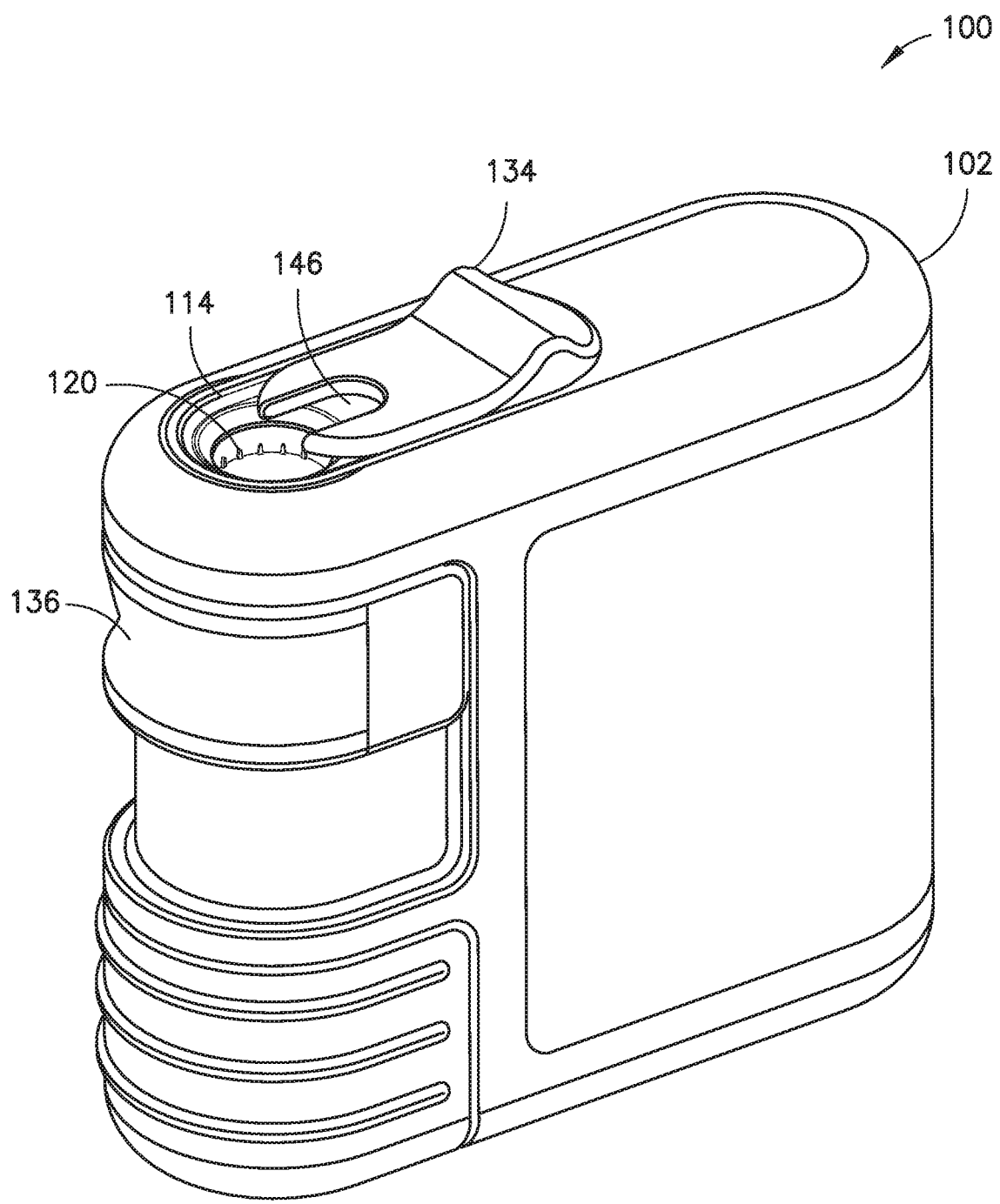
FIG. 1 is a perspective view of a medical sharp removal and storage device in accordance with an embodiment of the present invention.

It is an aspect of the present invention to provide device for entirely removing a medical sharp from a medical sharp holder and storing the removed medical sharp.

The foregoing and/or other aspects of the present invention are achieved by providing an apparatus for entirely removing a medical sharp from a holder to which it is connected, including a body, a heating unit disposed in the body, a receiving unit fixedly disposed in the body and configured to receive the holder, and a collet movably disposed within the body and configured to receive the medical sharp. The apparatus also includes a first biasing member disposed within the body, and a user interface coupled to the collet and configured to displace the collet away from the receiving unit, actuate the first biasing member to increase a bias on the collet toward the receiving unit, and actuate the heating unit.

The foregoing and/or other aspects of the present invention are also achieved by providing a method of entirely removing a medical sharp from a holder to which it is connected, including inserting a medical sharp and at least a portion of a holder to which it is connected into a receiving unit of a device, displacing a user interface in a first direction to pull the medical sharp in a first direction and activate an induction coil in the device, and maintaining a force on the user interface until the induction coil heats the medical sharp sufficiently to separate the medical sharp from the holder.

Additional and/or other aspects and advantages of the present invention will be set forth in the description that follows, or will be apparent from the description, or may be learned by practice of the invention.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected." "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 2:
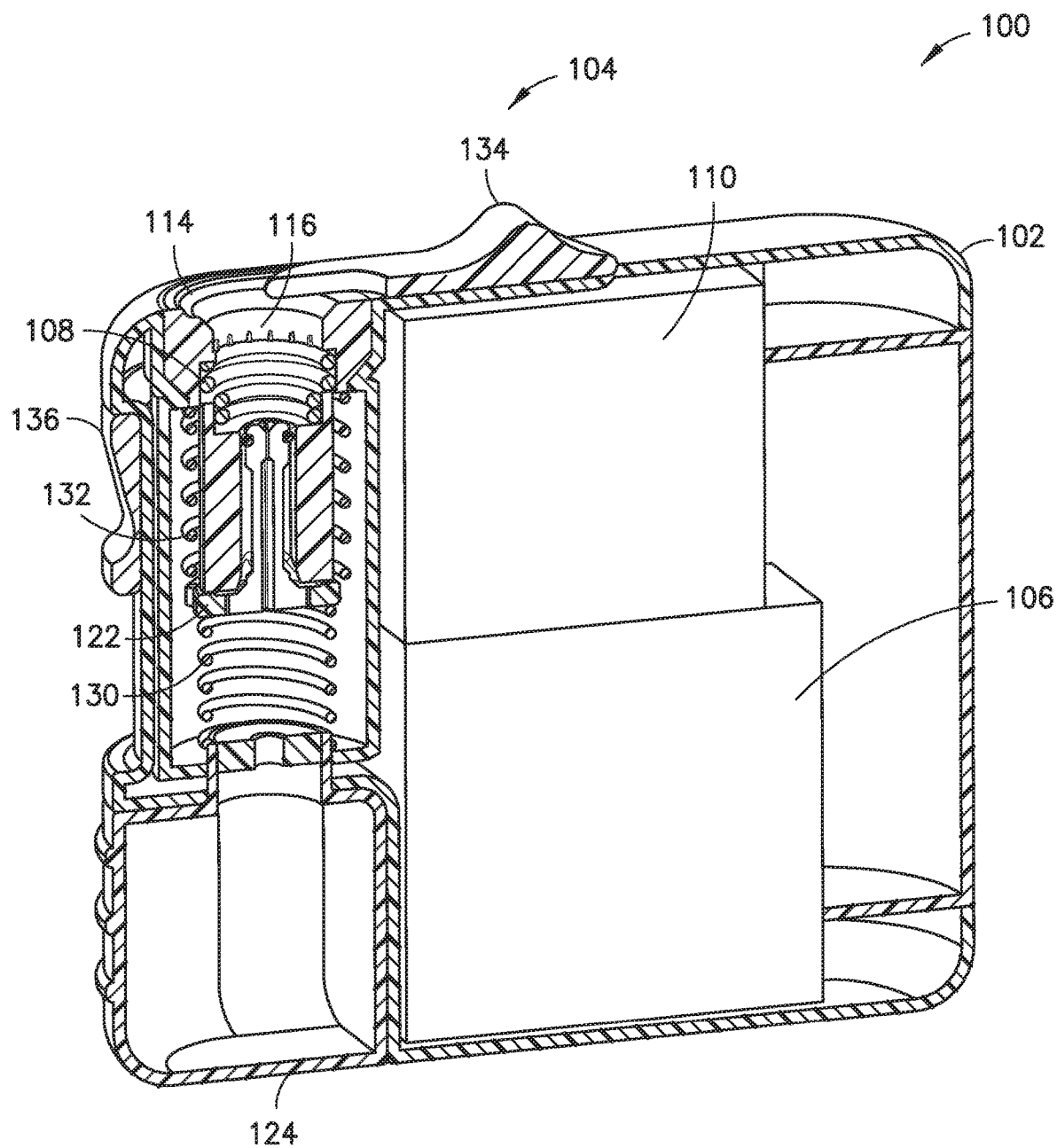
FIG. 2 is a cross-sectional view of the device of FIG. 1.

FIG. 1 is a perspective of a medical sharp removal and storage device 100 in accordance with an embodiment of the present invention, and FIG. 2 is a cross-sectional view of the device 100. As shown in the figures, the device 100 includes a body 102 and a heating unit 104. The electrical construction and operation of the device 100 is summarized below, but is described in more detail in a U.S. Provisional Patent Application Ser. No. 62/530,001, filed on Jul. 7, 2017, entitled "Induction Heating Circuit for Medical Sharps Removal Device." According to one embodiment, the heating unit 104 includes an energy source 106, such as a battery 106 or the like, an induction coil 108, and a controller 110, electrically connectable to the energy source 106 and the induction coil 108. The controller can include a printed circuit board, and can have circuit board components, such as a memory chip and a microprocessor.

Figure 19:
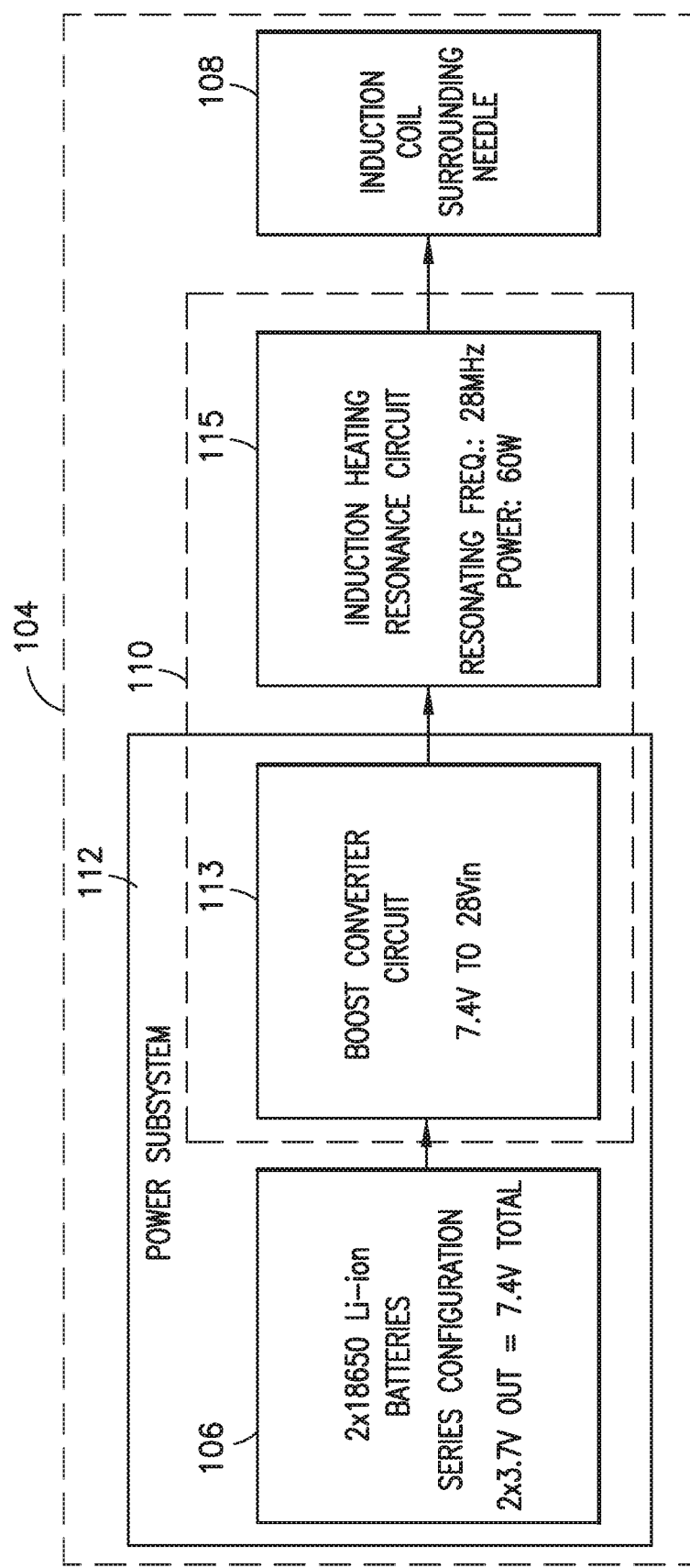
FIG. 19 is a block diagram of a heating unit of the device of FIG. 1.

As best shown in FIG. 19, the heating unit 104 can be additionally configured as a power subsystem 112 that includes the energy source 106 and a boost converter circuit 113. According to one embodiment, the boost converter circuit 113 and an induction heating resonance circuit 115 are part of the controller 110. In one embodiment, the energy source 106 includes a battery 106, such as one or more lithium-ion batteries configured in series (for example, two 3.7-volt batteries). One skilled in the art will appreciate that other battery configurations or other types of batteries can be employed without departing from the scope of the present invention. According to one embodiment, the energy source 106 is removable from the body 102, and is replaceable.

Referring back to FIG. 2, the device 100 also includes a receiving unit 114 fixedly disposed in the body 102, a collet 122, a sharps receiving container or chamber 124, first and second biasing units 130 and 132, a door member 134, and a slider or user interface 136. In one embodiment, the sharps receiving container 124 is removable from the body 102.

Figure 3:
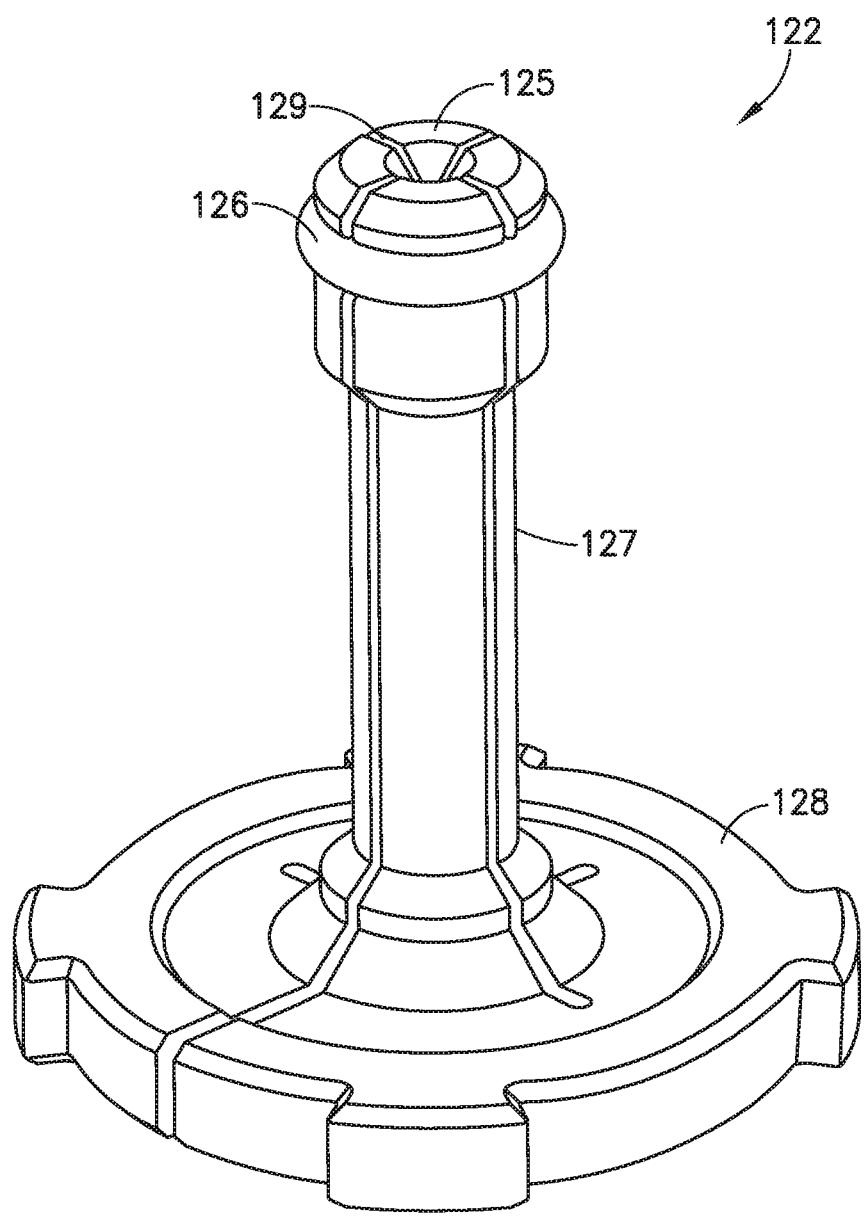
FIG. 3 is a perspective view of a collet of the device of FIG. 1.
Figure 4:
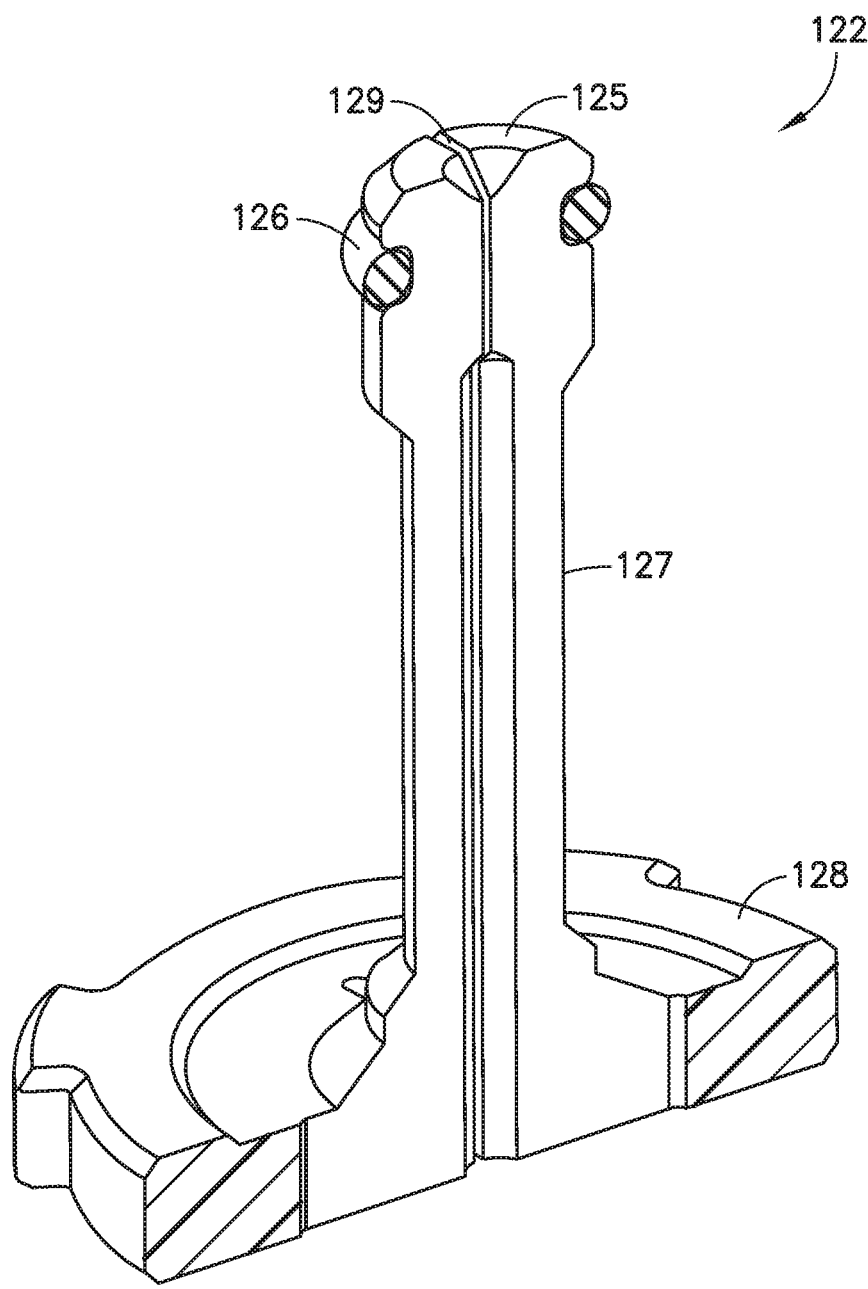
FIG. 4 is a cross-sectional view of the collet of FIG. 3.

FIG. 3 is a perspective view of the collet 122, and FIG. 4 is a cross-sectional view of the collet 122. The collet 122 includes a sharp receiving portion 125 for receiving the medical sharp, a collet biasing member or collet closing member 126 biasing the sharp receiving portion 125 radially inward to grasp the medical sharp, a radial flange 128, and a neck portion 127 connecting the flange 128 and the sharp receiving portion 125. According to one embodiment, the collet 122 includes a plurality of relief spaces 129 between sections of the collet that provide the collet 122 the ability to compress, for example, under the bias of the collet closing member 126. The relief spaces 129 also accommodate differently shaped medical sharps in the collet 122. One example of a collet closing member 126 is an elastic O-ring. Other collet closing members can be employed without departing from the scope of the present invention.

Figure 5:
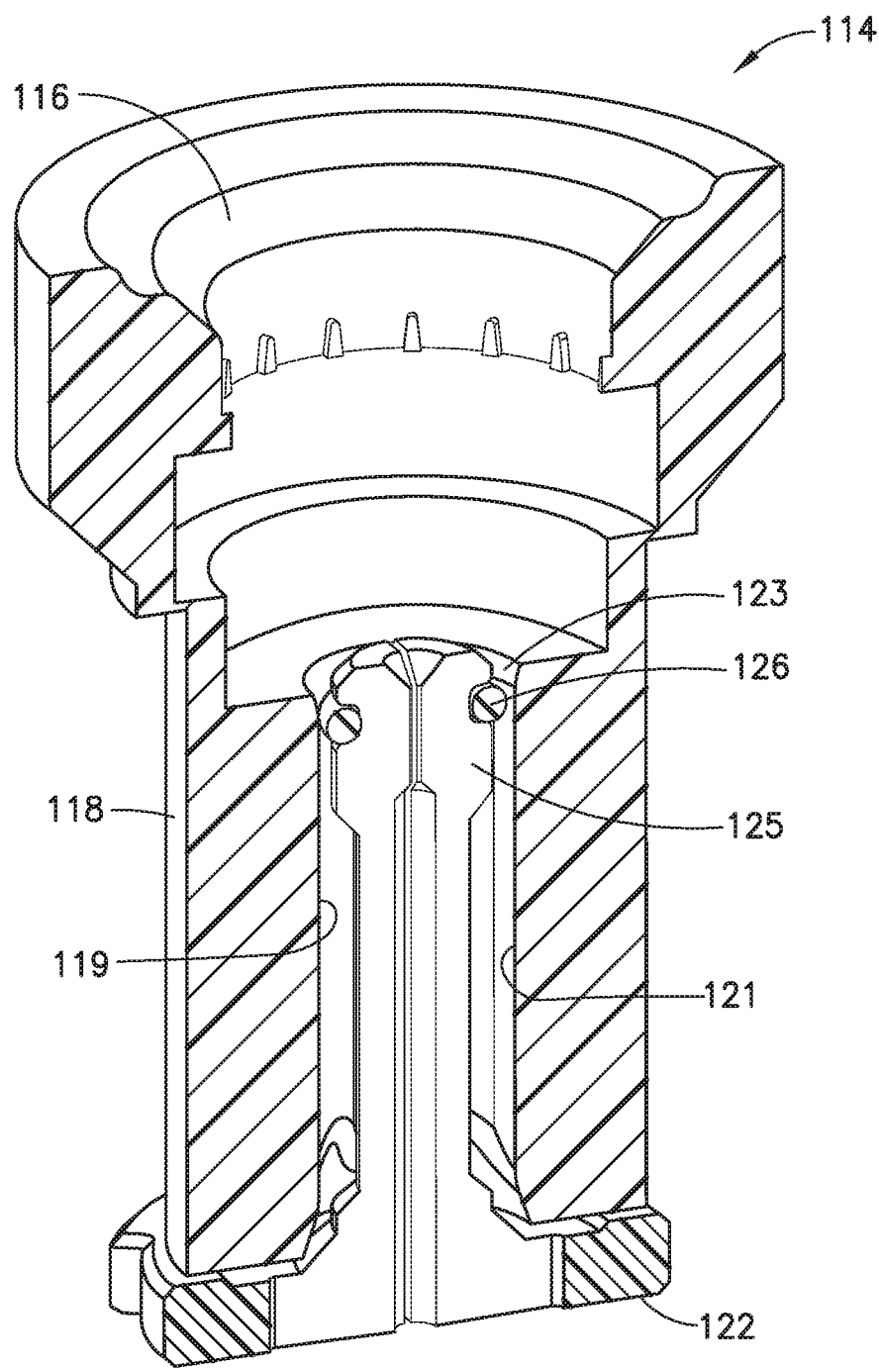
FIG. 5 is a cross-sectional view of the collet of FIG. 3 and a receiving unit of the device of FIG. 1.

FIG. 5 is a cross-sectional view of the collet 122 and the receiving unit 114. As shown in FIGS. 1, 2, and 5, the receiving unit has a receiving portion 116 with internal splines 120, and a columnar portion 118 extending from the receiving portion 116. As best shown in FIG. 5, and as subsequently described in greater detail, an interior of the columnar portion 118 has a straight section 119 and a tapered section or outwardly tapered section 121 that widens as it extends away from the receiving portion 116. According to one embodiment, adjacent to the receiving portion 116, the columnar portion 118 includes a chamfer, or inwardly tapered section 123.

When positioned as shown in FIG. 5, i.e., prior to the user interface or slider 136 being displaced, the straight section 119 of the interior of the columnar portion 118 radially compresses the collet. For example, preferably, the straight section 119 contacts the collet closing member 126 to further compress the sharp receiving portion 125 of the collet 122. In other words, according to one embodiment, the combination of the collet closing member 126 and the straight section 119 can compress the sharp receiving portion 125 of the collet 122 to a greater extent than the collet closing member 126 alone. Alternatively, in one embodiment, the collet closing 126 member is omitted, and the straight section 119 provides compression for the sharp receiving portion 125 of the collet 122.

Figure 6:
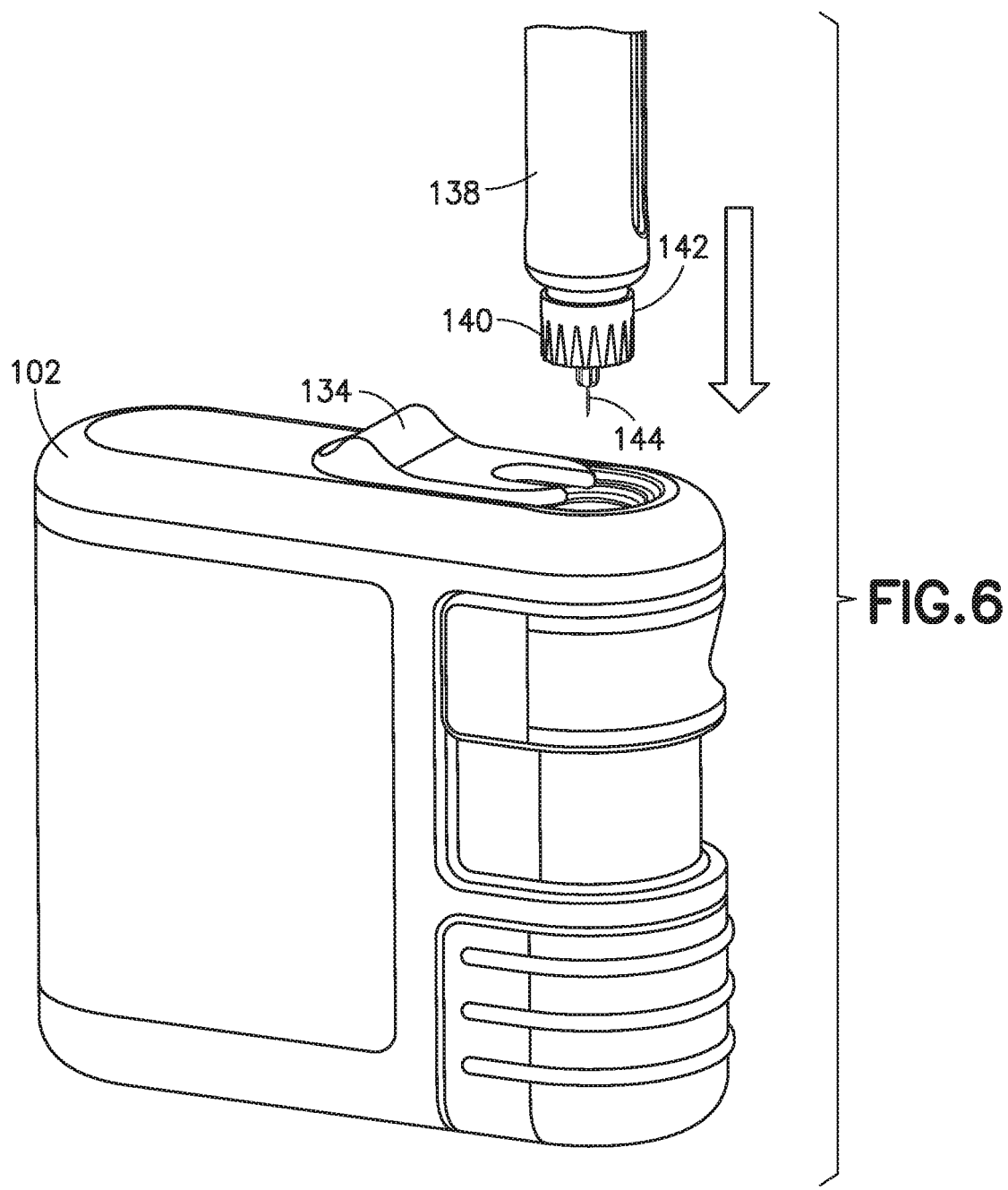
FIGS. 6-18 illustrate the operation of the device of FIG. 1.
Figure 7:
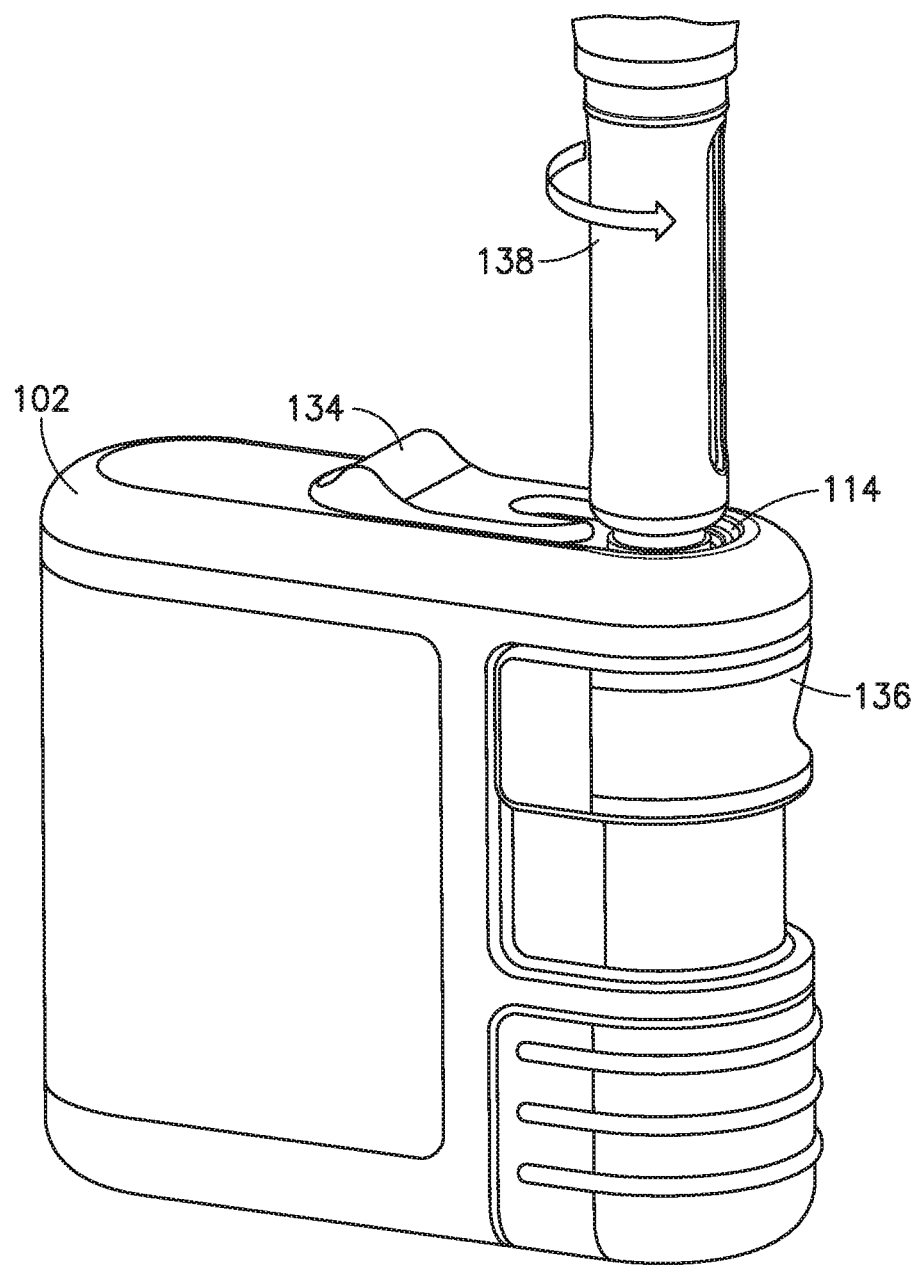
Figure 8:
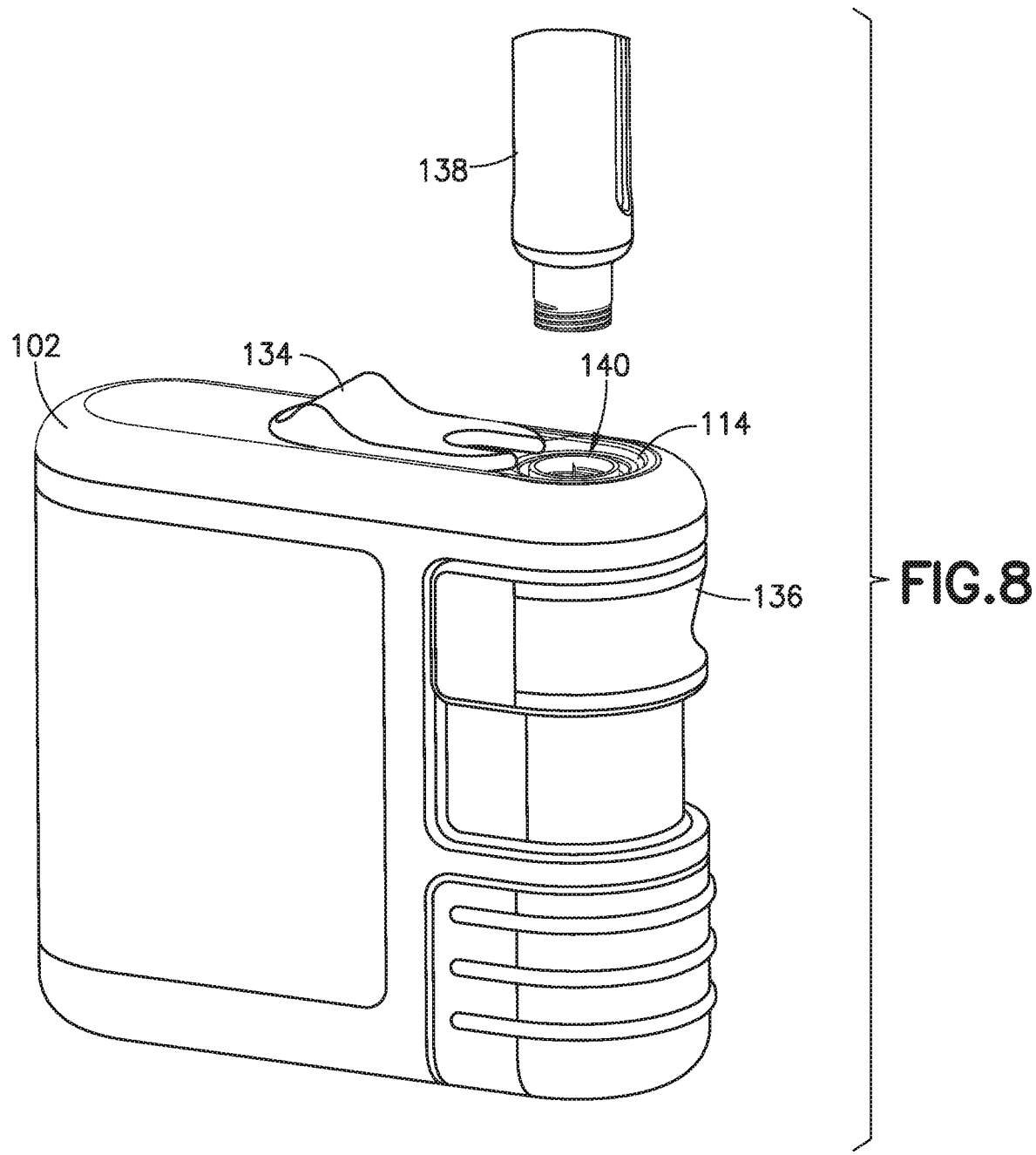
Figure 9:
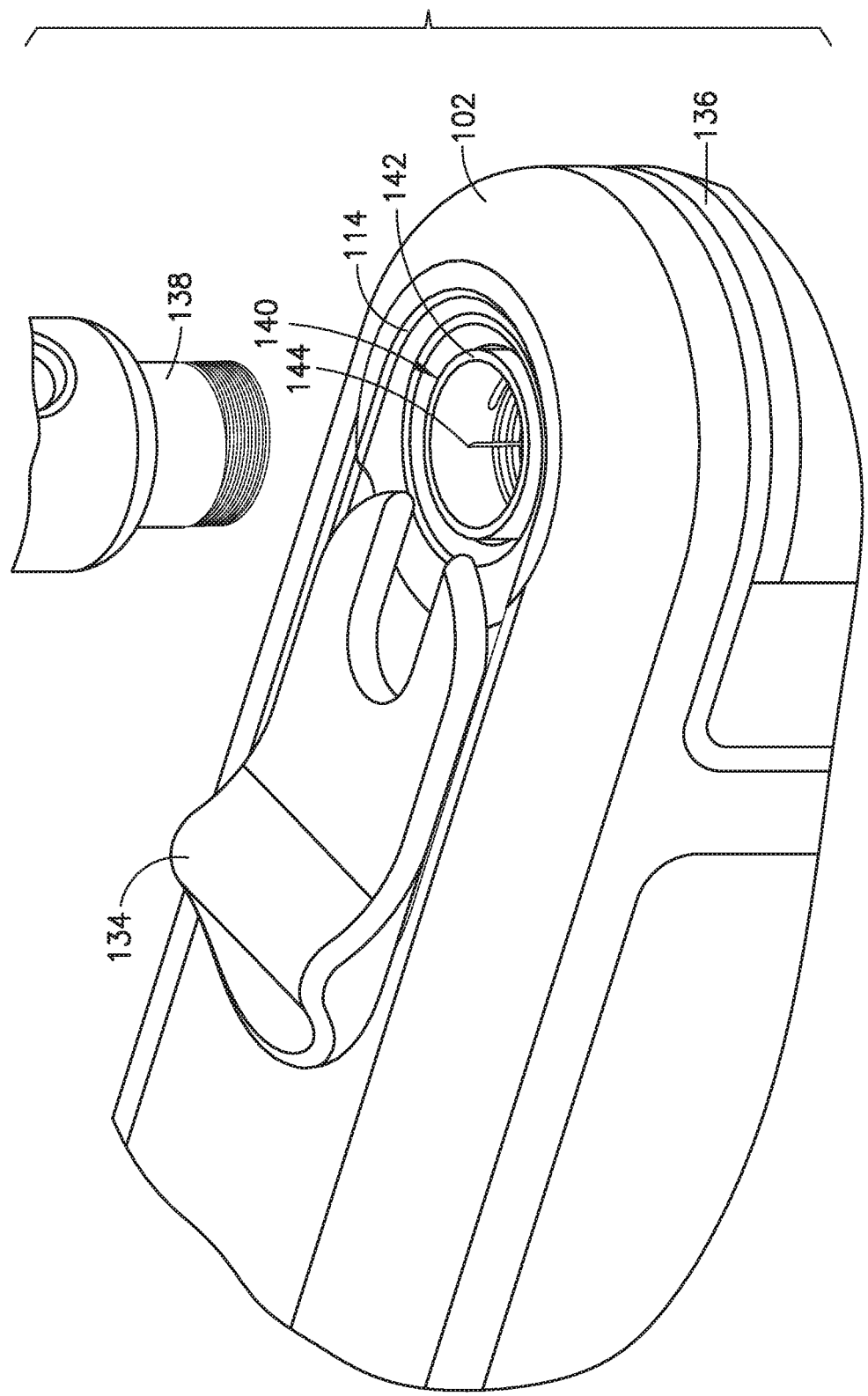

FIGS. 6-18 illustrate operation of the medical sharp removal and storage device 100. In FIG. 6, a user inserts a pen needle 140 connected to a pen injector 138 into the receiving portion 116 of the receiving unit 114. The pen needle 140 includes a hub 142 and a medical sharp or needle 144. The splines of the pen needle engage the internal splines 120 of the receiving portion 116 to resist rotation of the pen needle 140, so that the user can unscrew the pen injector 138 from the pen needle 140 (FIG. 7), and remove the pen injector 138, leaving the pen needle 140 in the receiving portion 116 of the receiving unit 114 (FIGS. 8 and 9).

When the user inserts the pen needle 140 into the receiving unit 114, the receiving portion 116 of the receiving unit 114 receives the hub 142, and the sharp receiving portion 125 of the collet 122 receives the needle 144. According to one embodiment, as the user inserts the pen needle 140 into the receiving unit 114, the collet closing member 126 permits the sharp receiving portion 125 to expand and grip the needle 144. According to another embodiment, in an initial receiving position, the collet 122 is open, and as the user inserts the pen needle 140 into the receiving unit 114, the open collet 122 receives the pen needle 140. In such an embodiment, the chamfer, or inwardly tapered section 123 assists with maintaining the collet 122 open in the initial receiving position, and, as subsequently described, as the collet 122 displaces away from the receiving unit 114, the collet 122 grips the needle 144. In both such embodiments, the contact between the straight section 121 of the interior of the columnar portion 118 and the collet closing member 126 and/or the sharp receiving portion 125 aids the sharp receiving portion 125 in gripping the needle 144.

Figure 10:
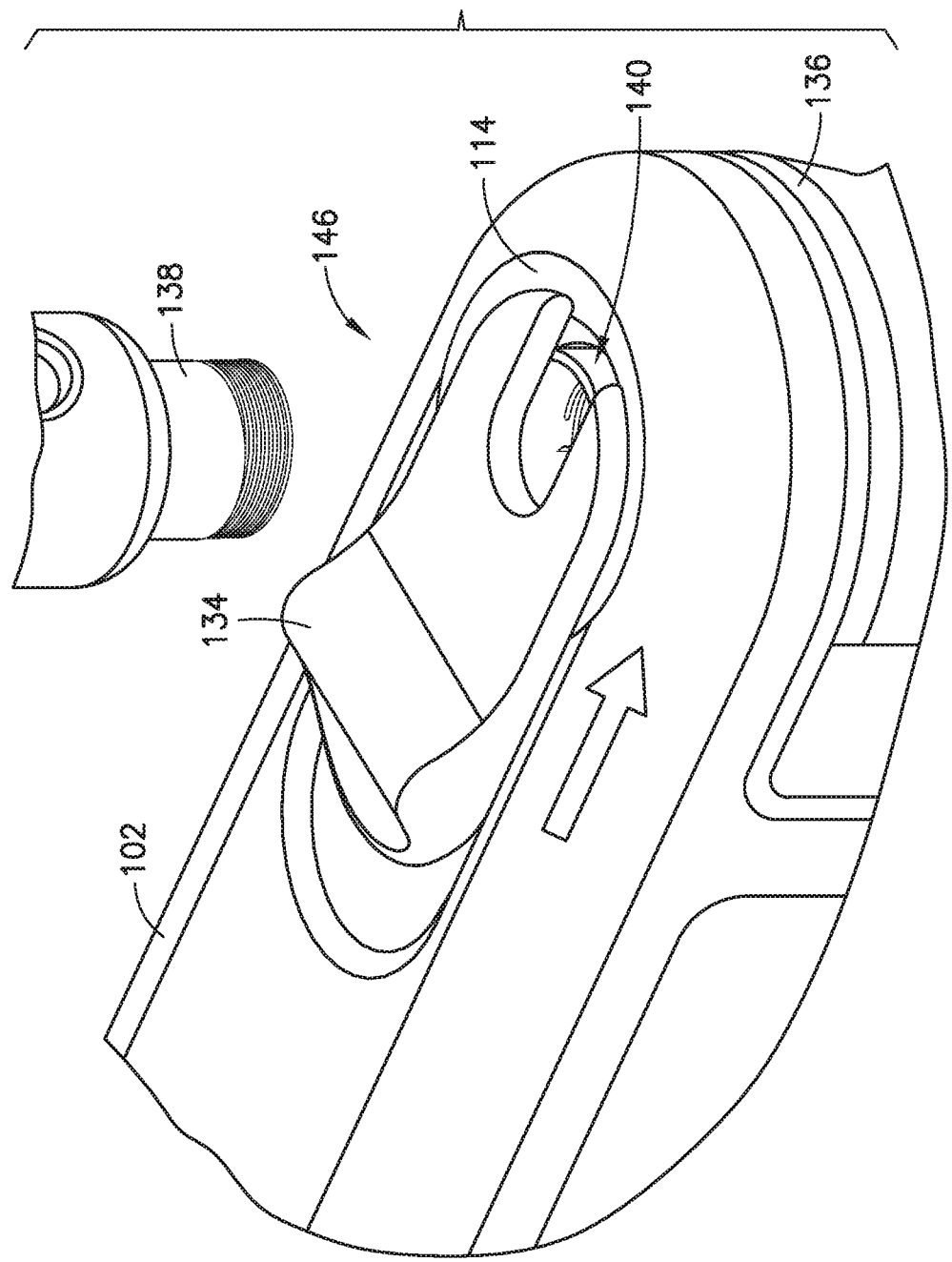
Figure 11:
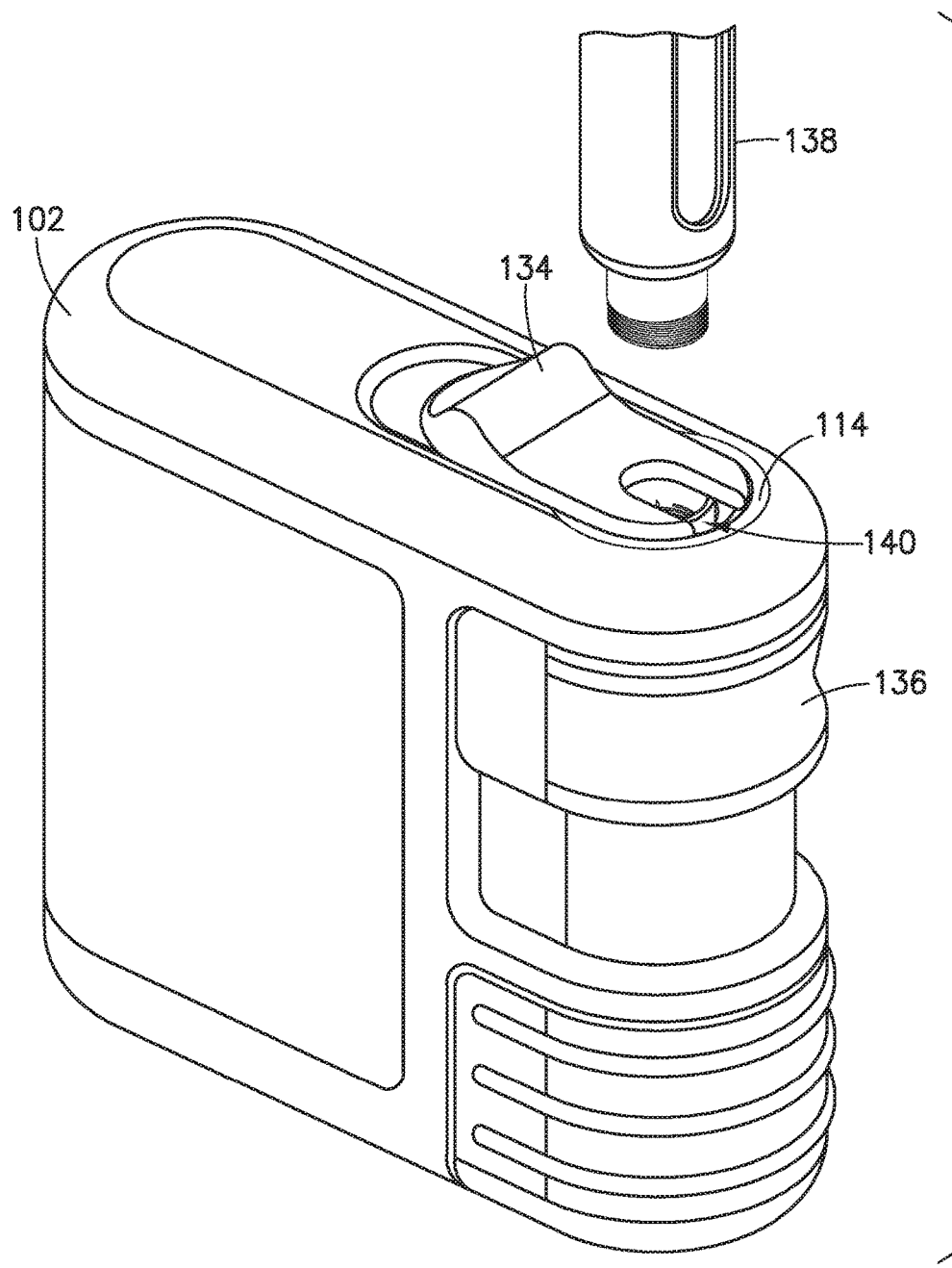

Subsequent to the user inserting the pen needle 140 into the receiving unit 114, as shown in FIGS. 10 and 11, the user closes the door member 134 by sliding the door member 134 forward relative to the body 102. This action preferably has two effects: first, the door member 134 aids in maintaining the pen needle 140 in the receiving unit 114; and second, the closed position of the door member 134 enables the controller 110 to energize the induction coil 108 via a door closure switch. For example, there can be a physical or optical sensor connected to the controller 110 that is triggered when the door member 134 reaches a closed position after a predetermined displacement relative to the body 102. Alternatively, the door member 134 can have an electrical contact that completes a portion of a circuit to between the controller 110 and the induction coil 108. Other methods of enabling the controller 110 to energize the induction coil 108 can be employed without departing from the scope of the present invention.

According to one embodiment, the door member 134 helps to block electro-magnetic interference (EMI) emissions, while also providing a lockout mechanism to assure that the pen injector 138 is not attached to the pen needle 140 during pulling of the needle 144. This assures that there is no chance of medication in the pen injector 138 being subjected to heat from the device 100. According to one embodiment, the previously-described door closure switch assures that the device 100 can only be operated with the door member 134 in the closed position (and the pen injector 138 removed).

Figure 12:
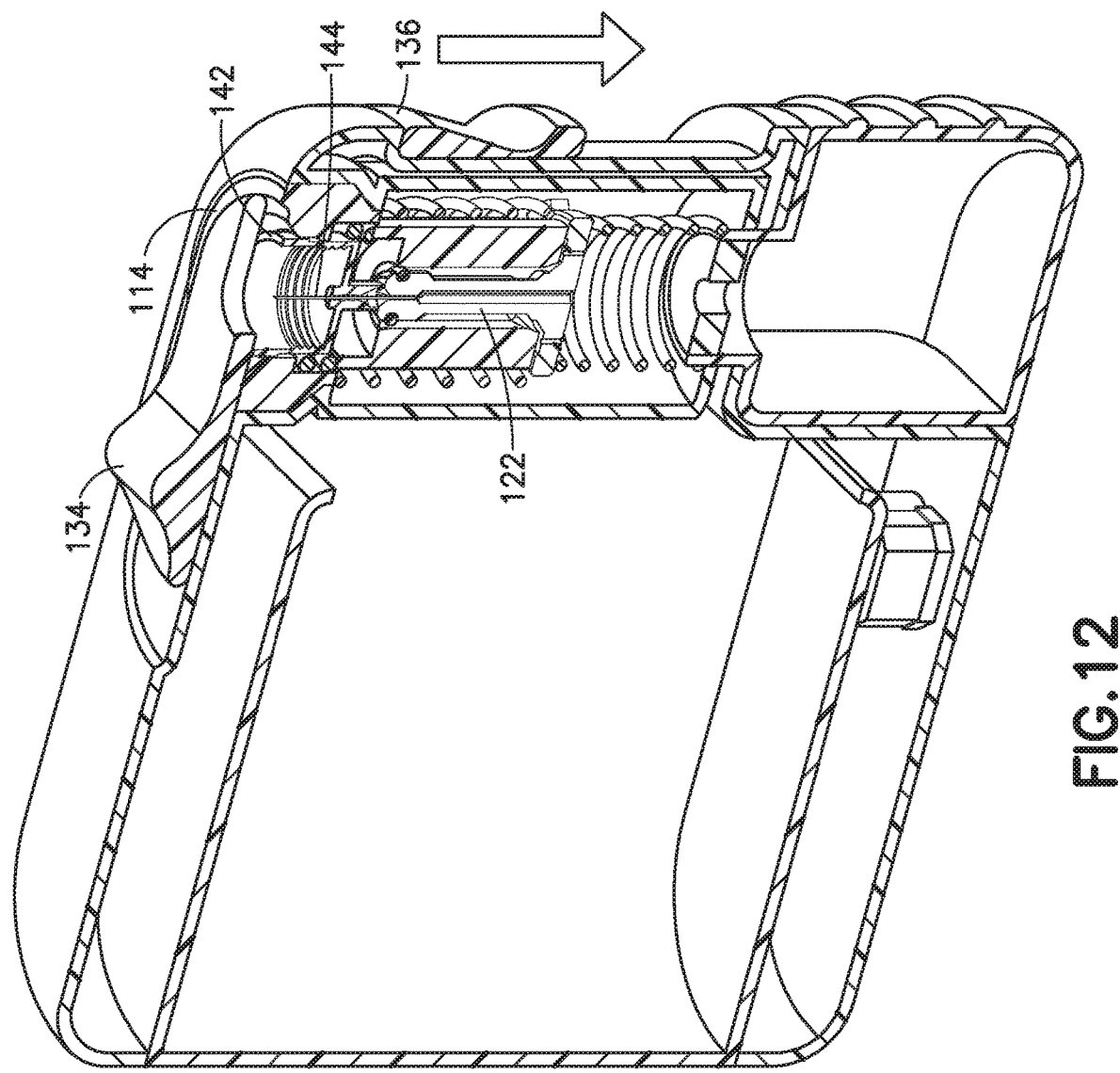
Figure 13:
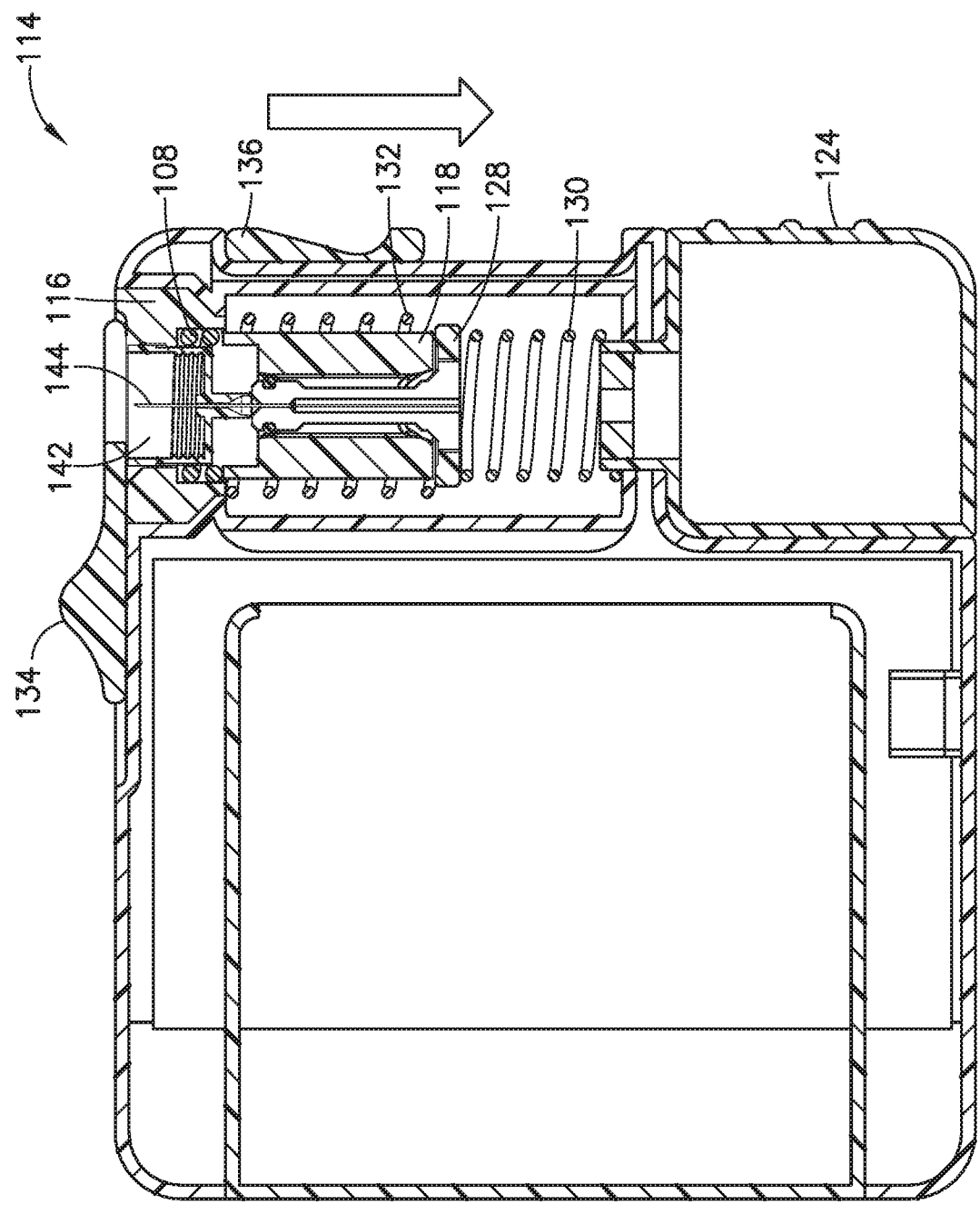

Subsequent to the user closing the door member 134, the user slides the slider or user interface 136 down in a first direction, as shown in FIGS. 12 and 13. Although the user interface 136 is depicted as the slider 136, one skilled in the art will appreciate that other user interfaces, such as a release button, can be employed without departing from the scope of the present invention. According to one embodiment, when the user moves the slider down in the first direction, this action closes the collet to grip the needle, while simultaneously energizing the coil.

As best shown in FIG. 13, the second biasing unit or spring 132 is disposed on top of the flange 128 and the first biasing unit or spring 130 is disposed beneath the flange 128. According to one embodiment, in the initial state shown in FIG. 13, prior to displacement of the collet 122, the first spring 130 biases the collet 122 toward the receiving unit 114. According to one embodiment, in the initial state shown in FIG. 13, the second spring 132 also biases the collet 122 away the receiving unit 114. According to one embodiment, in the initial state shown in FIG. 13, neither the first spring 130 nor the second spring 132 biases the collet 122. One skilled in the art will understand that by appropriately sizing the first and second biasing units 130 and 132, a desired force profile can be achieved for the force applied by a user on the slider 136 to operate the device 100.

The user interface or slider 136 is coupled to the collet 122. In one embodiment, the user interface or slider 136 is directly coupled to the collet 122. In another embodiment, another element, such as the second biasing unit or spring 132, is disposed between the user interface or slider 136 and the collet 122, and converts displacement of the slider 136 into displacement of the collet 122.

Displacement of the slider 136 by a predetermined distance causes the collet 122 to grip the needle 144 and also actuates the heating unit. According to one embodiment, the device 100 includes a mechanical or optical sensor connected with the controller 110 to determine when the predetermined displacement of the slider or user interface 136 has occurred, to signal the controller to complete the circuit and supply high-frequency electrical current to the induction coil 108. Alternatively, the slider or user interface 136 can have an electrical contact that completes the electrical circuit from the energy source 106 to the induction coil 108, enabling the controller 110 to control the supply of energy to the induction coil 108.

Supplying energy to the induction coil 108 generates an intense magnetic field in the middle of the induction coil. Because of the presence of the metal medical sharp, the magnetic field induces an electrical current and resultant heating in the metal medical sharp (e.g., the stainless steel needle 144). The heating softens and weakens the adhesive and/or the plastic connecting the medical sharp 144 with the holder 142 (in this example, hub 142). According to one embodiment, during the heating, the needle 144 reaches a temperature sufficient to sterilize the needle 144.

Figure 14:
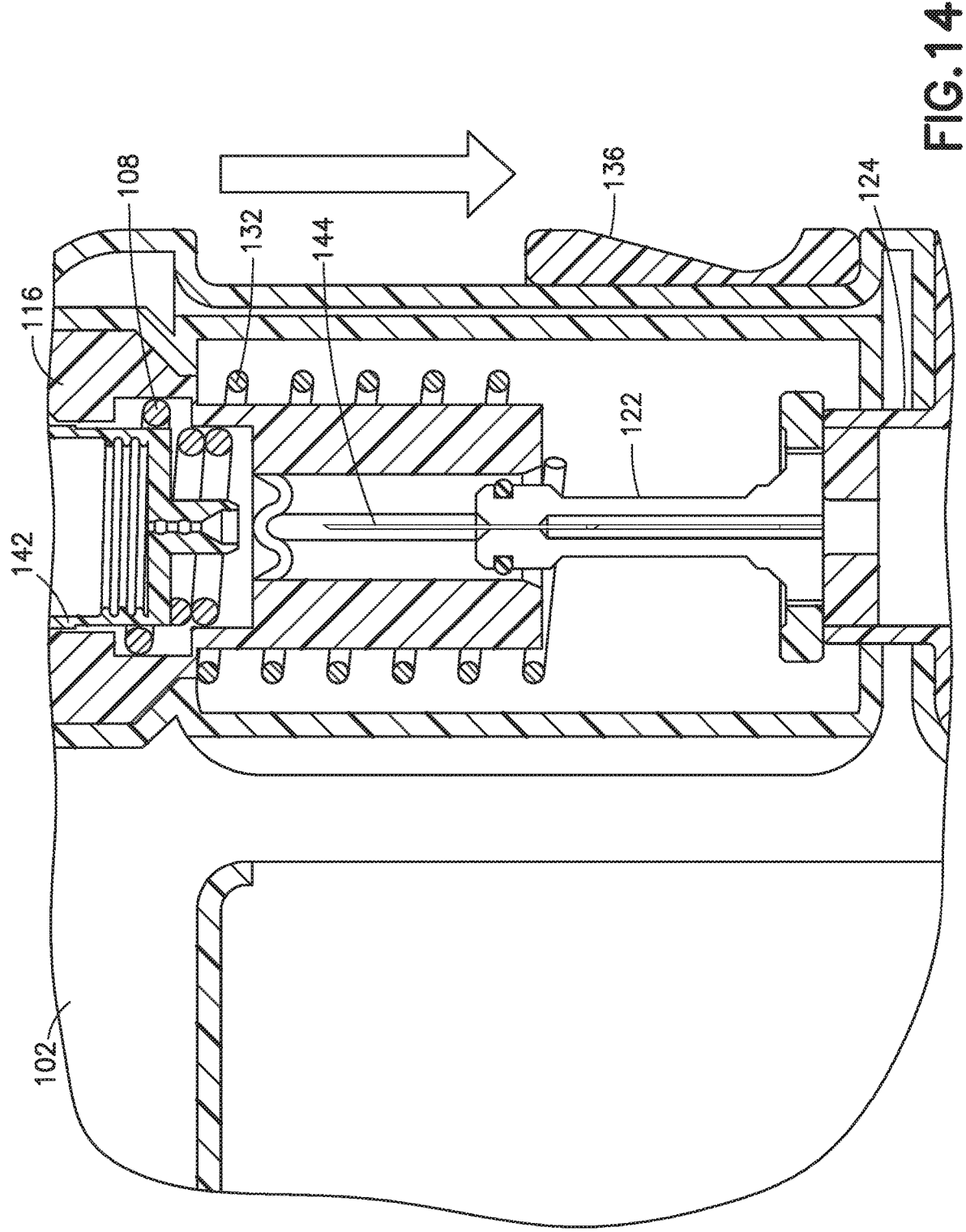
Figure 15:
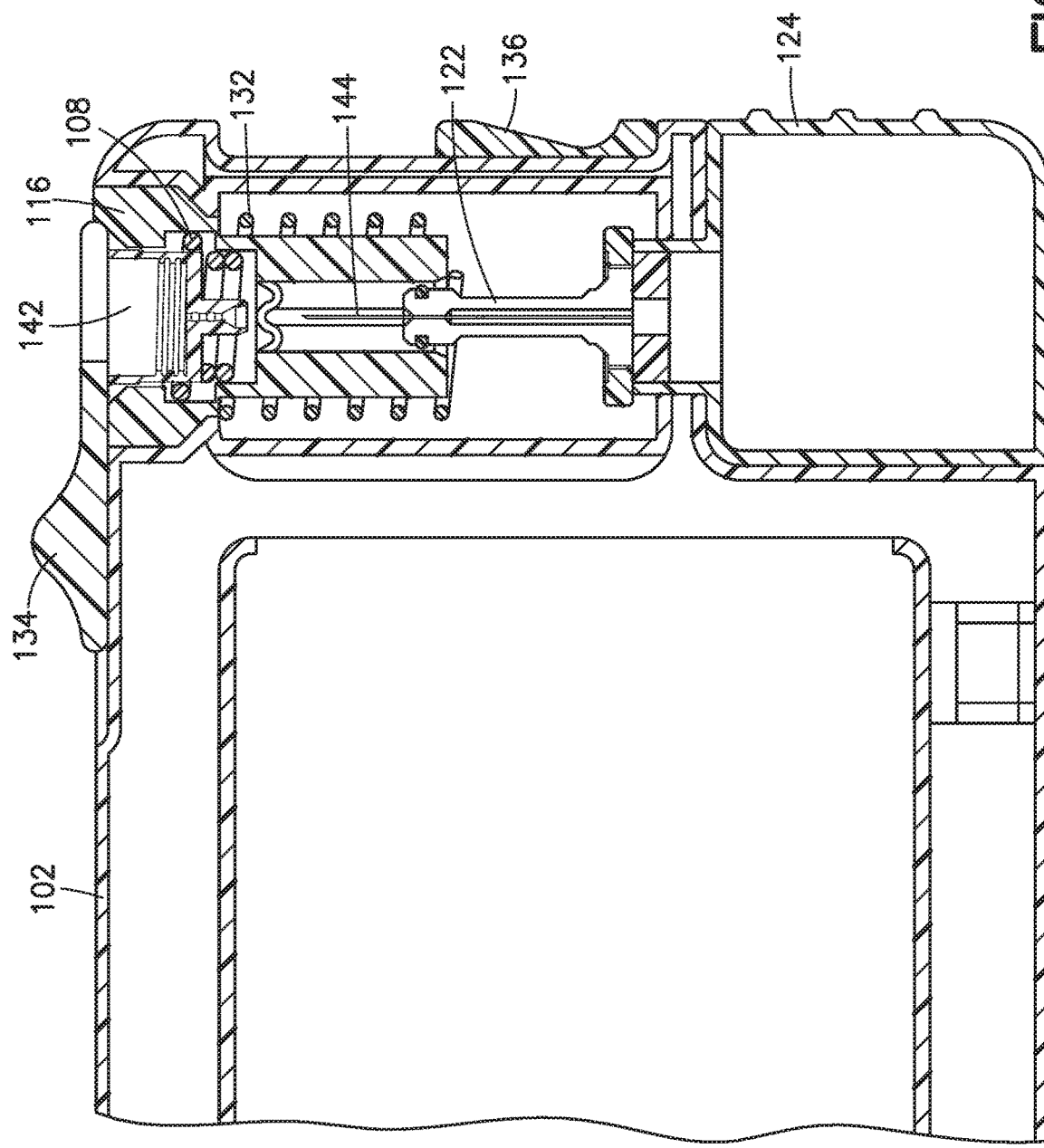
Figure 16:
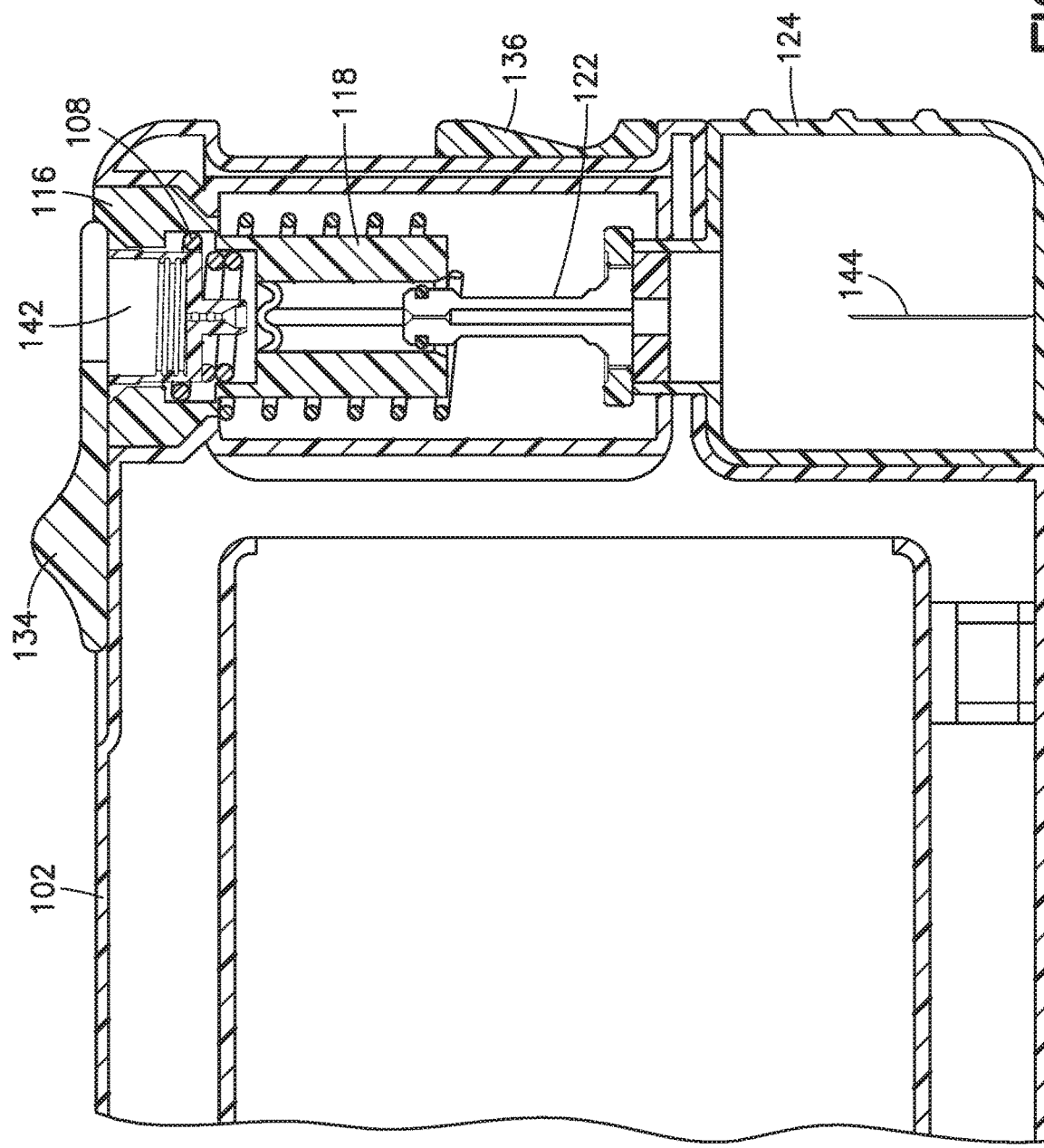

Because the collet 122 is being pushed down by the force applied by the user to the slider 136, once the connection between the needle 144 and the hub 142 is sufficiently softened and weakened by the induced heating to permit displacement of the needle 144 relative to the hub 142, the collet 122, which is still gripping the needle 144, pulls the needle 144 downward and free of the hub 142. As shown in FIGS. 14-16, as the collet 122 travels down in the first direction, because of the taper (downwardly increasing diameter) of the tapered section 121 of the interior of the columnar portion 118 of the receiving unit 114, the radially inward force applied to the sharp receiving portion 125 of the collet, and thus, the grip on the needle 144 decreases. In other words, the tapered shape of the tapered section 121 permits the collet to expand as it travels in the first direction (i.e., downward in the figures). Preferably, the location of the tapered section 121 relative to the location of the straight section 119 permits the collet 122 to expand and release the needle 144 only after the needle 144 has been fully pulled free from the hub 142.

According to one embodiment, the state in which the connection between the needle 144 and the hub 142 is sufficiently softened and weakened by the induced heating to permit displacement of the needle 144 relative to the hub 142 is achieved rather suddenly, and the collet 122 imparts momentum to the needle. Once the grip of the collet 122 decreases sufficiently, the collet 122 releases the needle 144, and the momentum of the needle 144 carries it into the sharps receiving container 124 (FIG. 16). In experiments, a needle has been pulled free from a hub in under two seconds. It is believed that a needle can be freed from a hub in less than one second, particularly if a non-metallic collet is employed. In terms of the user experience, the user applies a force and slides the user interface 136 a predetermined distance, there is a brief delay while applying the same force, and then the user interface 136 released to travel the rest of its path.

Figure 20:
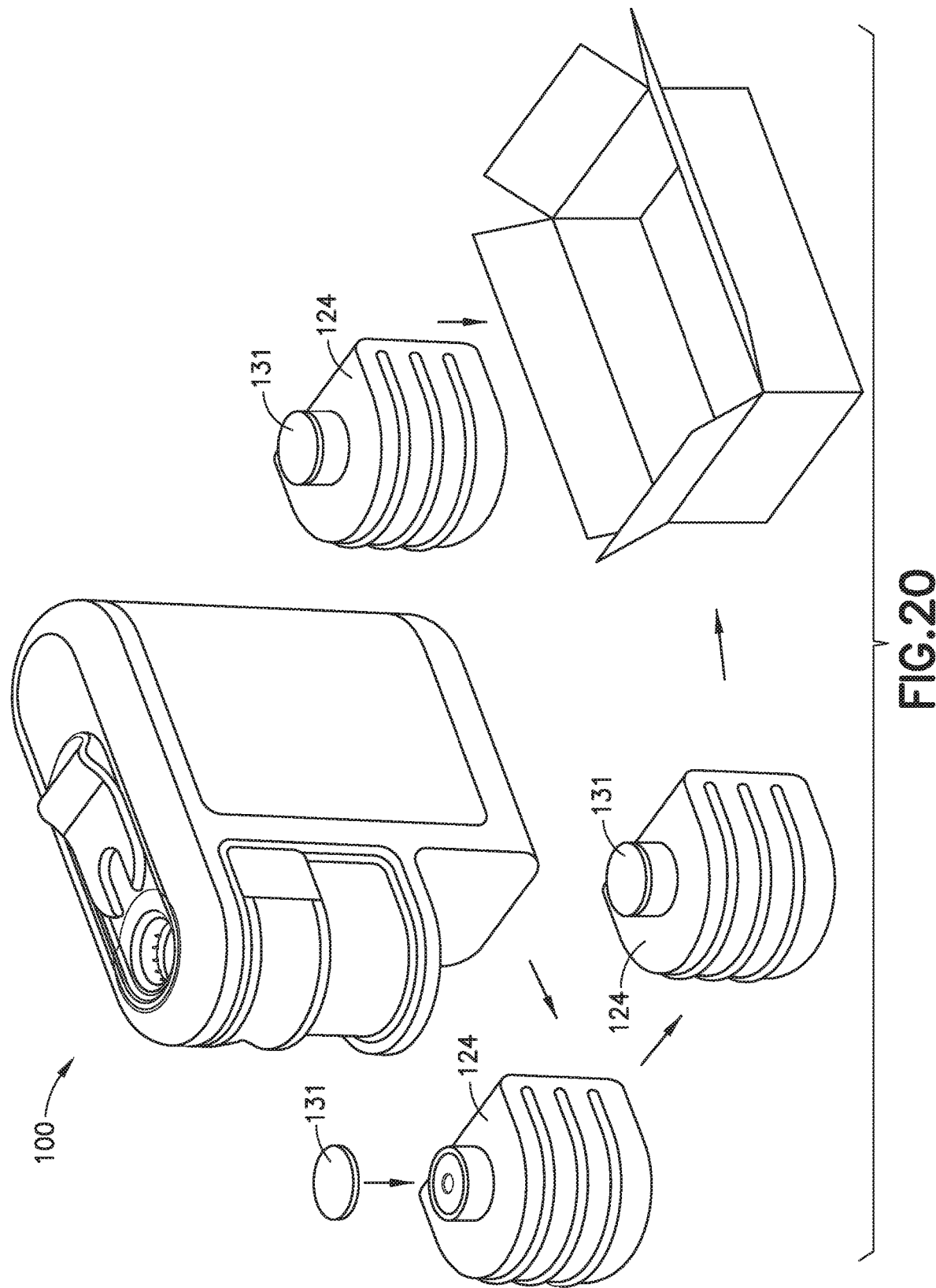
FIG. 20 illustrates removing a container of the device of FIG. 1 being removed, sealed, and mailed.

Preferably, the sharps receiving container 124 has an opening in the top with a rubber septum or valve (such as a duckbill valve). According to one embodiment, the septum or valve is opened by a wedge or cone when the sharps receiving container 124 is attached to the body 102, allowing the needle 144 to subsequently enter the sharps receiving container 124 as previously described. Preferably, when the sharps receiving container 124 is removed from the body 102, the septum or valve springs closed so that the needles 144 are retained and cannot fall out. Subsequent to container 124 being removed, as shown in FIG. 20, the container 124 can be sealed with a cap 131 (for example, a plastic cap) for disposal via different waste collection methods, such as a sharps mail back program.

Figure 17:
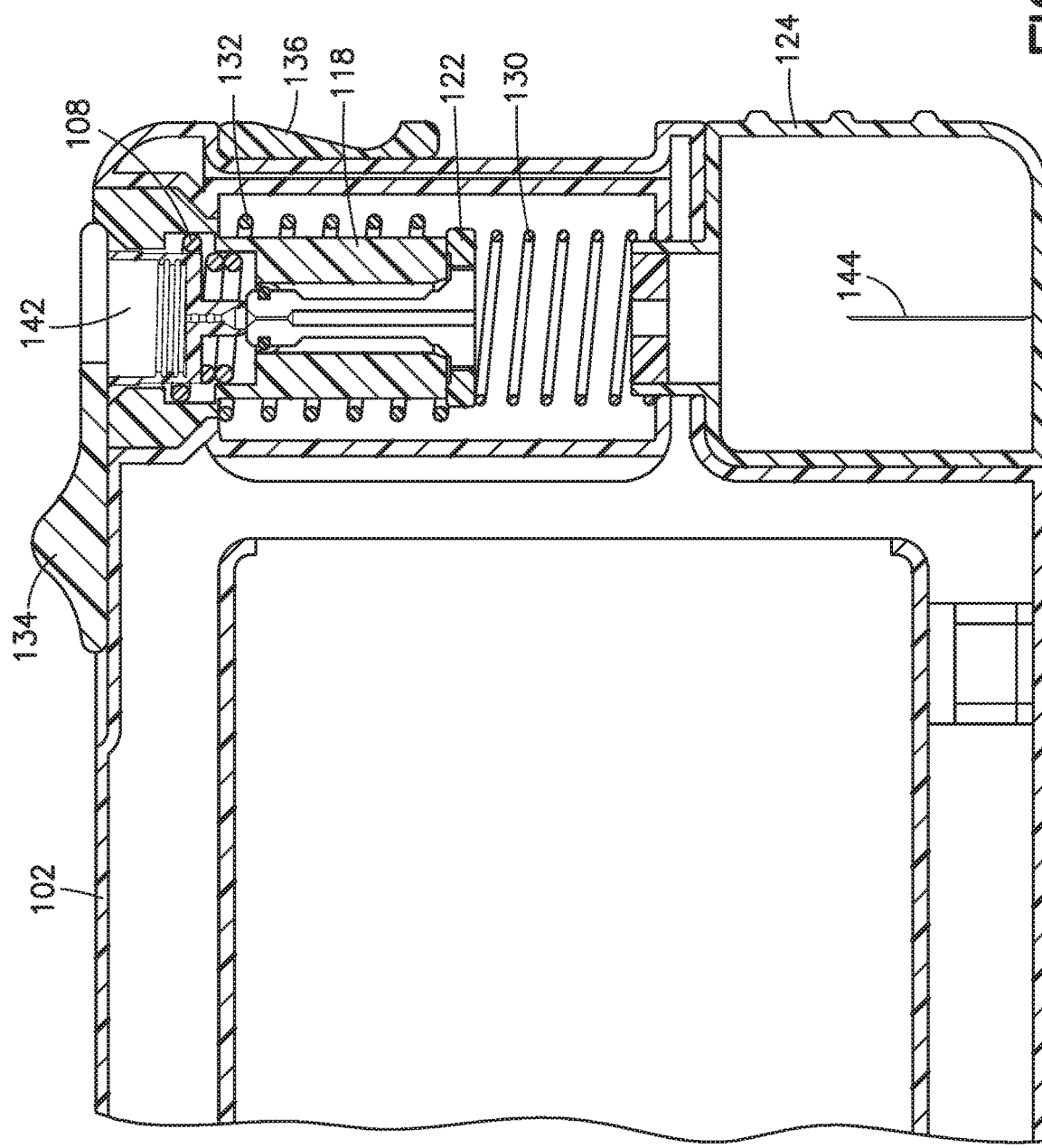

Once the needle 144 is disposed in the sharps receiving container 124, the user releases the downward force applied to the slider 136, and the first spring 130 returns the collet 122 and the slider 136 to the initial position shown in FIG. 17. Alternatively, the user can return the slider 136 (and thus the collet 122 due to their coupling) to the initial position shown in FIG. 17.

According to one embodiment, the controller 110 supplies energy to the induction coil 108 for a predetermined time. Alternatively, the controller can control the energy supply to the induction coil 108 based on the position of the slider 136 or the collet 122 (for example, via sensors or electrical contacts previously described or different sensors).

Figure 18:
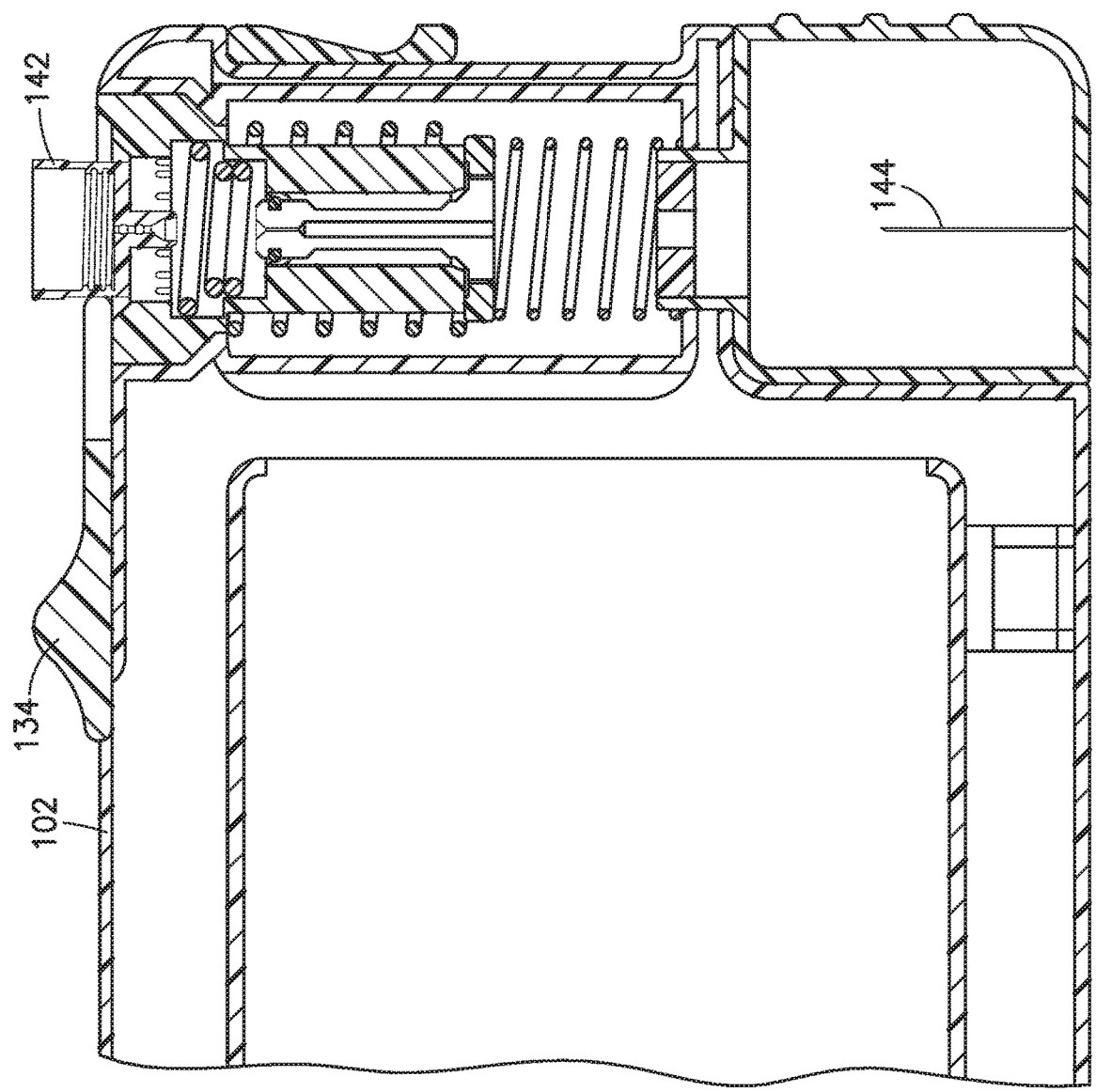

Once the needle 144 is separated from the hub 142, as shown in FIG. 18, the user can open the door member 134 and remove the hub 142 from the device 100 for disposal or recycling, while the needle 144 is safely disposed in the sharps receiving container or chamber 124.

In the illustrated example of FIGS. 6-18, the medical sharp is the needle 144 and the holder is the hub 142. But other medical sharps and holders can be separated using the device 100. For example, a lancet can be separated from its handle, a trocar can be separated from its handle, a needle can be separated from a staked syringe to which it is affixed, and a needle can be separated from a holder that is fitted to a syringe, or any medical device having a hazardous sharps component that needs to be separated from its plastic holder piece and contained for disposal. A door cutout 146 (see, e.g., FIGS. 1 and 10) in the door member 134 accommodates a lancet handle, a trocar handle and/or a syringe while the device 100 is used to separate the medical sharp from the holder, and still permit the door member 134 to close. Similarly, different shapes of receiving units may be utilized to accommodate different medical devices to provide a snug fit between the receiving unit and the holder/handle of the sharp. In other words, different devices 100 can have differently-shaped receiving units, each receiving unit being tailored to a different type of medical sharp. Alternatively, a plurality of interchangeable receiving units can be provided to accommodate different types of medical sharps in a single device 100. According to one such embodiment, the user can switch out the receiving unit (e.g., switch out or replace receiving unit 114 with receiving unit 141, as shown in FIG. 21) to accommodate the particular medical sharp.

The body 102, the receiving unit 114, the collet 122, the door member 134, the slider 136, and the sharps receiving container 124 can be made of plastic, such as polypropylene (PP), polyethylene (PE), polycarbonate (PC), acrylonitrile butadiene styrene (ABS), and polyether ether ketone (PEEK). Different components can be made of different plastics. Preferably, the collet 122 is ceramic, or is made of metal, such as aluminum.

Embodiments of the present invention with the induction coil are particularly useful in situations in which direct access to multiple contact points on the medical sharp are difficult (thereby making a conductive heating mechanism a less achievable), for example, a lancet, or a staked syringe, as previously described.

Embodiments of the present invention provide a portable personal sharps container/removal device that allows for safe containment and disposal of contaminated sharps, and can improve needle disposal compliance of needle users.

Embodiments of the present invention operate by removing only the sharps portion of the injection device (for example, pen needle or syringe but not limited thereto) and retaining the sharps portion inside the device while allowing the user to discard the plastic non-sharps component as regular trash or recyclable content. Embodiments of the present invention achieve this effect by generating an area of intense high-temperature near, for example, the adhesive bead that adheres the medical sharp to the holder, in conjunction with a "pull-out" mechanism.

The separation of the sharp from its holder can be achieved in several ways, such as by melting all or part of the sharp, by locally heating the sharp so that it can be more easily cut or broken, by using the heated sharp to soften or melt an adhesive that attaches the sharp to its holder, or by using the heated sharp to soften or melt the adjoining plastic material of the holder itself. These methods can be used alone or in combination with each other, and can also be used in combination with mechanical separation methods. In some embodiments of the present invention, the heating can be achieved by an induction heating mechanism. With such a mechanism, the needle does not need to be directly contacted by the heating mechanism. The heating can also be achieved in other ways, such as a heating element directly contacting the medical sharp, or contacting the medical sharp to complete an electrical circuit to pass a current through the medical sharp.

In some embodiments of the present invention, the device has a durable component and a disposable component. The durable component utilizes a power source, such as a battery (rechargeable or otherwise). An indicator can be incorporated into the device that alerts the user when the cannula holding compartment or sharps receiving container 124 has reached a certain capacity. A similar feature can used to manage power requirements, such as battery replacement or recharging. The disposable component (chamber or sharps receiving container 124) can be utilized until an adequate number of needles has been introduced into the chamber, after which it can be detached and disposed of appropriately.

Appropriate disposal can include a variety of options, for example, the disposable component can be mailed to the manufacturer or a separate waste management entity, or the disposable component can be thrown away in an appropriate medical disposal receptacle. Preferably, replacement disposable components can be obtained to continue using the durable component for subsequent medical sharps removal.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. An apparatus for entirely removing a medical sharp from a holder to which it is connected, comprising:
   a body;
   a heating unit disposed in the body;
   a receiving unit fixedly disposed in the body and configured to receive the holder;
   a collet movably disposed within the body and configured to receive the medical sharp;
   a first biasing member disposed within the body; and
   a user interface coupled to the collet and configured to displace the collet away from the receiving unit, actuate the first biasing member to increase a bias on the collet toward the receiving unit, and actuate the heating unit.

2. The apparatus according to claim 1, wherein the receiving unit comprises:
a receiving portion configured to receive the holder; and
a columnar portion extending from the receiving portion in a first direction;
wherein collet travels within the columnar portion, and the columnar portion compresses the collet during at least a portion of a travel path of the collet.

3. The apparatus according to claim 2, wherein a section of the columnar portion is tapered to widen in the first direction.

4. The apparatus according to claim 2, wherein a section of the columnar portion is shaped to reduce a force applied by the columnar portion to the collet as the collet travels in the first direction.

5. The apparatus according to claim 1, wherein the heating unit comprises:
an energy source;
an induction coil;
and a controller, configured to control the energy source to supply energy to the induction coil.

6. The apparatus according to claim 5, wherein the induction coil is disposed about the receiving unit.

7. The apparatus according to claim 1, further comprising a second biasing member disposed between the user interface and the collet, configured to bias the collet away from the receiving unit.

8. The apparatus according to claim 1, further comprising a collet closing member biasing the collet toward a closed state.

9. The apparatus according to claim 1, wherein the receiving unit comprises internal splines configured to grip a pen needle, to aid removal of the pen needle from an injection pen.

10. The apparatus according to claim 1, further comprising a door member movably disposed on the body and configured to contact the holder and enable operation of the heating unit.

11. The apparatus according to claim 1, wherein displacing the user interface in a first direction biases the collet to displace the collet in the first direction, actuates the first biasing member to increase the bias of the collet toward the receiving unit, and actuates the heating unit.

12. The apparatus according to claim 11, wherein upon the heating unit heating the medical sharp sufficiently to loosen a connection between the holder and the medical sharp, the collet displaces in the first direction, removing the entire medical sharp from the holder, and releases the medical sharp.

13. A method of entirely removing a medical sharp from a holder to which it is connected, comprising:
inserting a medical sharp and at least a portion of a holder to which it is connected into a receiving unit of a device;
displacing a user interface in a first direction to pull the medical sharp in a first direction and activate an induction coil in the device; and
maintaining a force on the user interface until the induction coil heats the medical sharp sufficiently to separate the medical sharp from the holder.

14. The method according to claim 13, wherein inserting the medical sharp and at least the portion of the holder further comprises inserting the medical sharp into a collet that grips the medical sharp and is coupled to the user interface.

15. The method according to claim 14, wherein displacing the user interface in the first direction further comprises displacing the collet in the first direction and actuating a biasing member to increase a bias on the collet toward the receiving unit.

16. The method according to claim 13, further comprising:
securing the medical sharp and the holder with respect to a body of the device.

17. The method according to claim 16, wherein securing the medical sharp and the holder comprises sliding a door to secure the medical sharp and the holder with respect to the body and enable actuation of the induction coil.

18. The method according to claim 13, further comprising:
releasing the force on the user interface; and
removing the holder from the device for disposal or recycling of the holder.

19. The method according to claim 18, further comprising mailing the holder to a manufacturer or a waste management entity.

20. The method according to claim 13, further comprising:
collecting one or more separated medical sharps in a container in the device;
removing the container from the device;
sealing the container; and
mailing the holder to a manufacturer or a waste management entity.

21. The method according to claim 13, further comprising:
switching out the receiving unit of the device for a receiving unit corresponding to a different type of medical sharp.

22. The method according to claim 13, wherein inserting the medical sharp and the at least portion of the holder to which it is connected into the receiving unit comprises inserting a pen needle assembly into the receiving unit.

23. The method according to claim 13, wherein inserting the medical sharp and the at least portion of the holder to which it is connected into the receiving unit comprises inserting a lancet and at least a portion of its holder into the receiving unit.

24. The method according to claim 13, wherein inserting the medical sharp and the at least portion of the holder to which it is connected into the receiving unit comprises inserting a syringe and at least a portion of its holder into the receiving unit.

* * * * *